US005505203A

United States Patent [19]
Deitrich et al.

[11] Patent Number: 5,505,203
[45] Date of Patent: Apr. 9, 1996

[54] METHOD AND APPARATUS FOR AUTOMATIC TRANSDUCER SELECTION IN ULTRASOUND IMAGING SYSTEM

[75] Inventors: Thomas L. Deitrich, Durham, N.C.; Michael J. Washburn, New Berlin, Wis.

[73] Assignee: General Electric Company, Milwaukee, Wis.

[21] Appl. No.: 344,055

[22] Filed: Nov. 23, 1994

[51] Int. Cl.$^6$ .................................................. A61B 8/00
[52] U.S. Cl. ........................................ 128/660.01; 73/607
[58] Field of Search ........................ 128/660.01, 662.03; 73/607, 606

[56] References Cited

U.S. PATENT DOCUMENTS

| | | | |
|---|---|---|---|
| 4,726,230 | 2/1988 | Yoshikawa et al. | 73/607 |
| 4,811,740 | 3/1989 | Ikeda et al. | 128/660.01 |
| 5,318,027 | 6/1994 | Fukui | 128/660.01 |

*Primary Examiner*—George Manuel
*Attorney, Agent, or Firm*—Dennis M. Flaherty; John H. Pilarski

[57] ABSTRACT

A method and an apparatus for activating one of a plurality of connected transducers in response to the operator picking up that transducer. This enables the selection of a transducer without the need for pressing a button or key. Automatic selection is accomplished by placing a proximity sensor located within the holder of the transducer or on the transducer itself to indicate whether the transducer is being held by its holder. Switches are also incorporated to detect when a transducer connector has been plugged into each port on the ultrasound imaging machine. Depending on the order in which unactivated normal transducers attain a state whereby the respective normal transducer is both connected and out of its holder, a stack of probe identifiers is created. Identifiers for connected special transducers are added to the stack below any probe identifiers for normal transducers. The identifier at the top of the stack indicates the transducer which will be activated next, i.e., after the presently active transducer has been deactivated. Identifiers are removed from the stack if the corresponding transducer is disconnected from the system or placed in its holder.

20 Claims, 4 Drawing Sheets

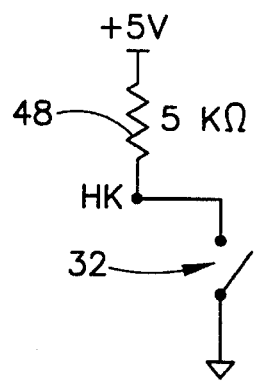
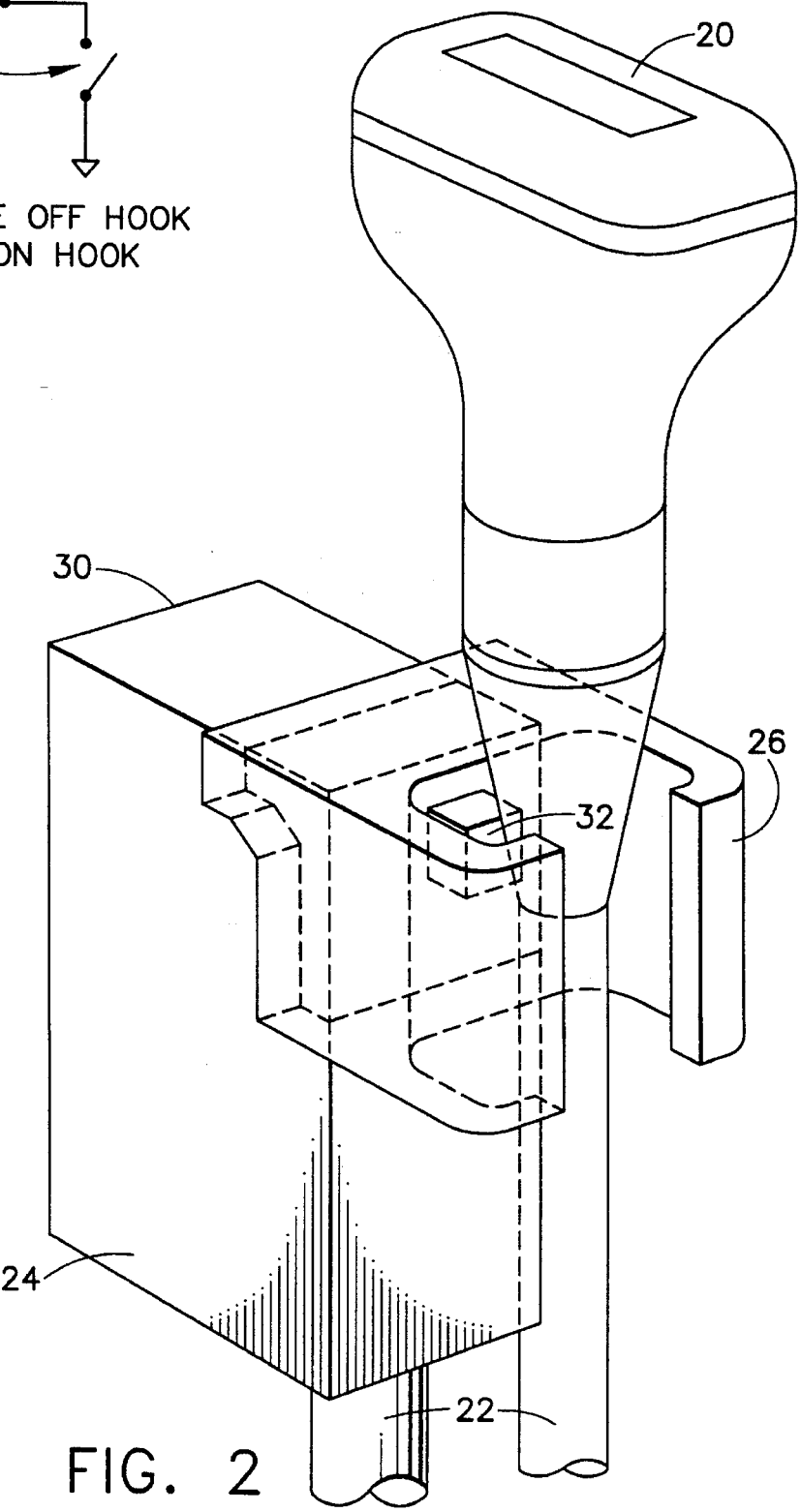
CLOSED: PROBE OFF HOOK
OPEN: PROBE ON HOOK
FIG. 3
FIG. 2

METHOD AND APPARATUS FOR AUTOMATIC TRANSDUCER SELECTION IN ULTRASOUND IMAGING SYSTEM

FIELD OF THE INVENTION

This invention generally relates to ultrasound imaging of human tissue and blood. In particular, the invention relates to means for activating a selected one of a plurality of transducer probes connected to an ultrasound imaging system.

BACKGROUND OF THE INVENTION

Conventional ultrasound imaging systems have interchangeable transducer probes which are suitable for different applications. The transducer family may, for example, consist of four types of transducers: phased array, linear, convex and specialty (i.e., transducers designed for imaging specific body parts). Each transducer probe is coupled to a respective port of the ultrasound imaging system via a coaxial cable and a transducer connector. The transducer connectors are interchangeable in the sense that each connector can be plugged into any port. The console of the system is also conventionally provided with a set of yokes for holding the respective transducers when they are not being used. This set of yokes is typically placed on the side of the main unit or under the operator console of the main unit.

Each transducer probe is designed for a specific application. Depending on the desired application, the appropriate probe must be connected and activated before it can be used to scan the anatomy of interest. If four different transducer probes are plugged into the console, the user must select one of the four for the scanning operation.

Previous implementations of transducer selection require the user of the machine to select or activate one of the connector ports and thereby energize the transducer connected thereto by pressing a button or key. The specified probe then begins to image in response to that selection. The user must pick up the transducer from its holder either before or after selecting it via the button or key in order to apply it to the patient and actually begin scanning.

The foregoing implementation requires the user to know which transducer is connected to which port and then press the appropriate key corresponding to the picked-up transducer. When an operator wishes to use a particular probe on a multi-probe imaging unit, usually the operator must trace the transducer probe to its particular connector via the coaxial cable in order to determine which port the transducer connector is connected to. Thus, there is a need for a transducer activation scheme which allows the user to activate a desired transducer by the simple act of picking up the transducer.

SUMMARY OF THE INVENTION

The present invention is a technique for automatically selecting one of a plurality of transducers for activation without the need for the operator to press any button or key. In particular, the transducer selection scheme in accordance with the invention selects the transducer to be activated solely on the basis of feedback indicating which ports of the ultrasound imaging system having transducer connectors plugged therein and which yokes are holding transducers.

In accordance with the invention, one of a plurality of connected transducers is activated in response to the operator picking up that transducer. Automatic selection is accomplished by placing a probe switch within the yoke or on the transducer to indicate when the transducer is being held by its holder. The transducer connectors also incorporate switches which indicate when the transducer connector has been plugged into a port on the console of the ultrasound imaging machine. Depending on which transducers are connected to the imaging system and which of those connected transducers are being held in their respective holders, the system controller determines which transducer should be activated and outputs the appropriate control signals to the probe activation circuitry on the transducer interface board.

BRIEF DESCRIPTION OF THE DRAWINGS

FIG. 2 is a block diagram of a transducer interface by which a plurality of transducer probes can be interfaced to an ultrasound imaging system.

FIG. 3 is a concept drawing of an integral yoke/transducer connector used in conjunction with the present invention.

DETAILED DESCRIPTION OF THE PREFERRED EMBODIMENTS

Figure 1:
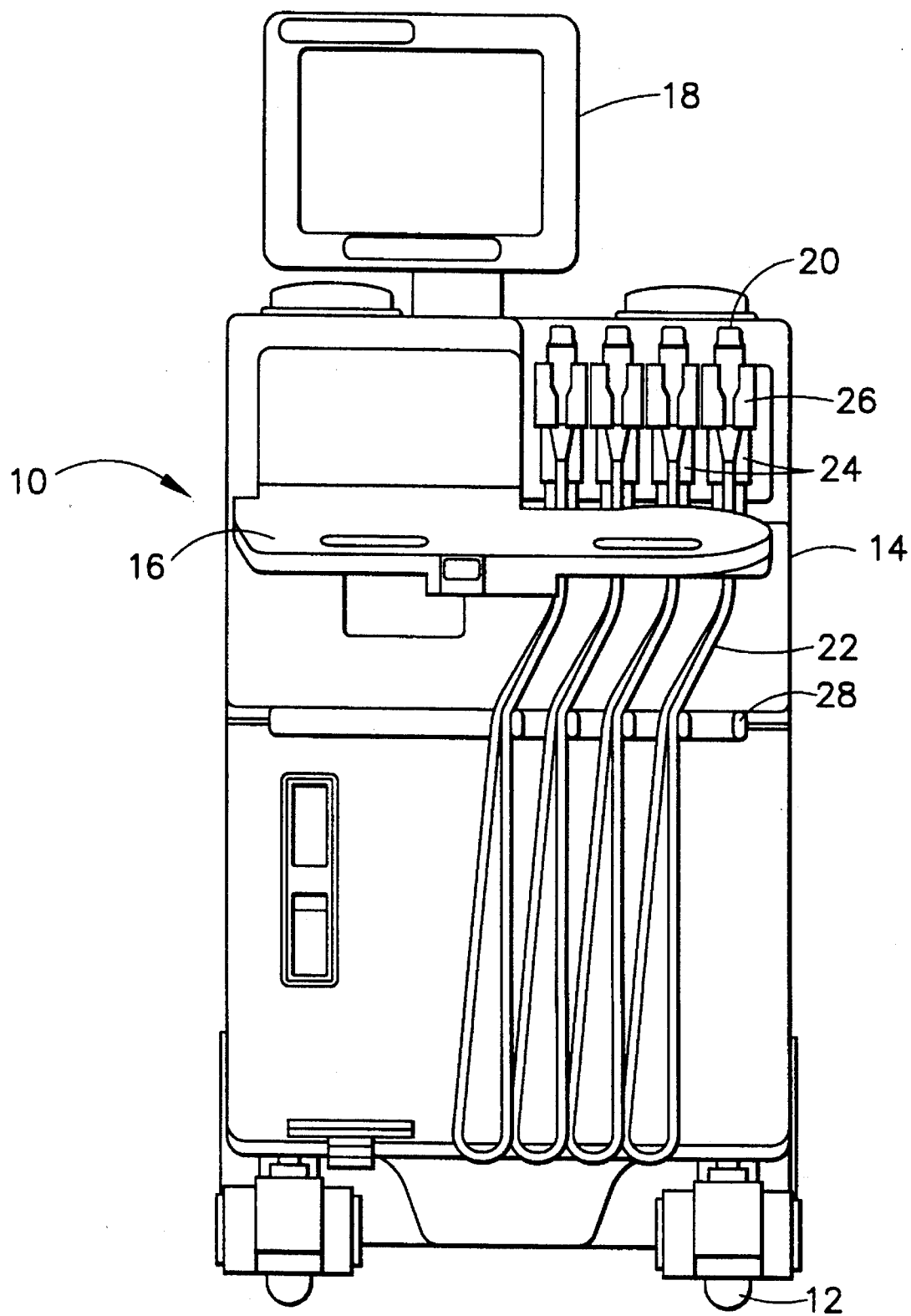
FIG. 1 is a front view of an ultrasound imaging unit having a plurality of interchangeable probe assemblies.

FIG. 1 shows an ultrasound imaging system having a plurality of interchangeable transducer probes. The system comprises a mobile main unit 10 which is transportable on a plurality of wheels 12. The main unit includes a housing 14, an operator console 16 and a display monitor 18. The housing 14 has a plurality of ports (not shown) by means of which a plurality of transducer probes 20 can be coupled to the signal processing subsystems located inside housing 14. Typically each probe is designed to meet the requirements of a specific application. The transducers fall into four general categories: phased array, linear, convex and specialty (i.e., transducers designed for imaging specific body parts).

Each transducer probe is coupled to a respective port of the ultrasound imaging system via a coaxial cable 22 and a transducer connector 24. The transducer connectors are interchangeable in the sense that each connector can be plugged into any port.

A set of yokes 26 are provided for holding the respective transducers when they are not being used, as shown in FIG. 1. Each yoke is attached to a corresponding transducer connector. The transducer probe, coaxial cable, connector and yoke form a transducer probe assembly. If the operator wishes to connect a different probe to the system, an entire probe assembly is removed and replaced by the new probe assembly.

The structure of the integral yoke/transducer connector is shown in detail in FIG. 2. The transducer probe 20 has an array of transducer elements (not shown) which transmit ultrasound in a transmission mode and receive ultrasound echoes from the anatomy being examined in a reception mode. The signal electrodes of the transducer elements are electrically connected to one end of respective conductive wires (not shown) of the coaxial cable 22. The other end of the conductive wires of coaxial cable 22 are electrically connected to circuitry inside the connector box 30. The connector circuitry is in turn electrically connected to the port (not shown) in which it is plugged. That port is electrically connected to a transducer interface board (described in detail below with reference to FIG. 4).

A probe switch 32 is incorporated in the integral yoke/transducer connector. This probe switch functions as a means of telling the system when the probe 20 has been lifted out of the probe holder or yoke 26. The probe switch 32 supplies a simple "on" and "off" passive response (single pole, single throw). The switch is closed when the probe is off the yoke and open when the probe is on the yoke. The circuit schematic for the probe switch is shown in FIG. 3.

The present invention utilizes the signal produced by the probe switch in determining the next transducer probe to be activated. In particular, the invention comprises means for forming a stack of probe identifiers having an order which is determined by the order in which unactivated normal transducers attain a state of being both connected and out of their respective holder. This stack is maintained by the system controller, which cooperates with the transducer interface 34 shown in FIG. 4. Up to four transducer probes can be connected to the imaging system via transducer connectors 24a–24d. When any one of the transducer connectors is plugged into a corresponding port in the imaging system, a Probe Present signal is produced which is stored in the probe present register 36.

As described above, each connector 24a–24d has a probe switch 32 (as shown in FIGS. 2 and 3) for indicating whether the corresponding probe is coupled to the corresponding yoke. The resulting probe switch hook status signal is input into the system via a pin labeled HK (see FIG. 3) on the transducer connector. This pin is pulled high by a 5 kΩ resistor 48 (see FIG. 3) on the transducer interface board 34. A transducer probe will either leave the pin floating, or ground the pin to form a signal indicating that the probe has been removed from its hook. The resulting probe switch hook status signal is stored in the probe switch hook status register 38.

In addition, each transducer type has a unique 8-bit probe ID. There are 8 pins labeled PTY 0 to PTY 7 on the transducer connector. These pins are pulled high by 5 kΩ resistors on the transducer interface board 34. A transducer will either leave the pins floating, or ground them to form its unique probe ID. The probe ID signals are stored in probe ID register 40.

Depending on the contents of registers 36, 38 and 40, a system controller 42 outputs a Probe Select signal to the probe activation circuitry 44 on the transducer interface board 34. Probe activation circuitry 44 activates the selected transducer probe in response to that Probe Select signal.

The present invention can be used in conjunction with a transducer selection control program stored in system controller 42. The system controller periodically reads the contents of registers 36, 38 and 40 and processes the retrieved information in accordance with a stored algorithm to select a transducer for activation. The Probe Select signal sent to the probe activation circuitry 44 identifies the selected transducer. The selected transducer is activated by the probe activation circuitry 44 via the associated transducer connector. Radiofrequency data from the transducer element array is then multiplexed, under the control of the system controller, from the transducer connector to the beamforming circuitry (not shown) via the RF data lines 54 on the transducer interface board 34.

In accordance with the preferred embodiment of the invention, the system controller maintains a so-called "transducer stack" stored in memory and comprising a list of identifiers of connected transducer probes to be activated. This stack does not include the identifier of the transducer which is presently activated, but rather only the identifiers of transducers in the order in which they will be activated in the future. The order in which transducer probes are to be activated is determined by the position of the probe identifier in the stack. For example, the probe designated by the identifier stored at the top of the stack has the highest priority and the probe designated by the identifier stored at the bottom of the stack has the lowest priority.

Figure 5:
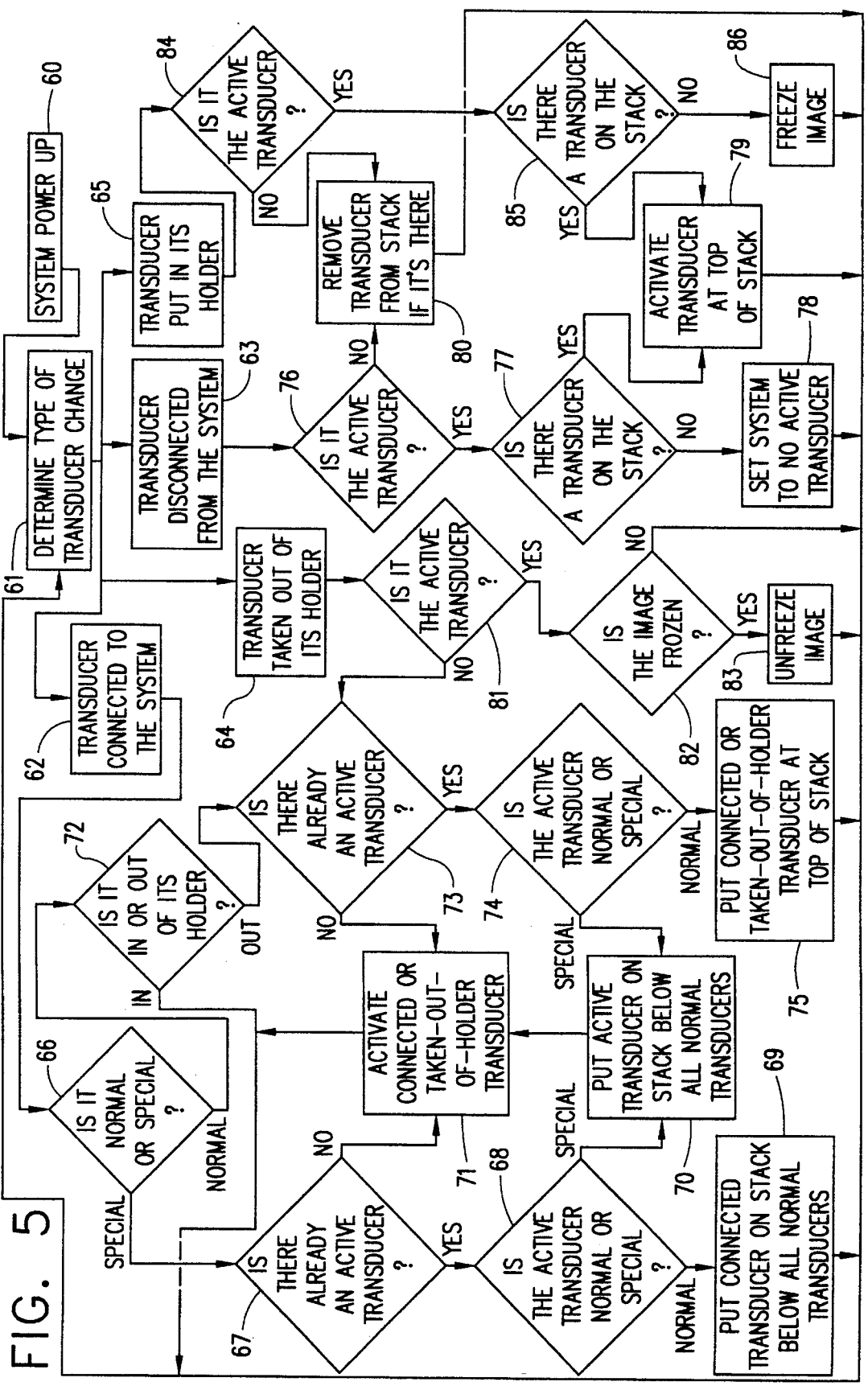
FIG. 5 is a flowchart depicting the sequence of steps which are automatically performed by the system controller to select a transducer for activation in accordance with a preferred embodiment of the invention.

The details of the algorithm used by the system controller to select a transducer to be activated are depicted in FIG. 5. To understand the transducer selection sequence, the following terms require definition: "Active Transducer" refers to the transducer with which the system is presently imaging; "Normal Transducer" refers to any transducer having a probe switch incorporated in its holder; "Special Transducer" refers to any transducer which does not have a probe switch incorporated in its holder; "Transducer In Holder" refers to a normal transducer in its holder; and "Transducer Off Holder" refers to a normal transducer out of its holder.

Figure 4:
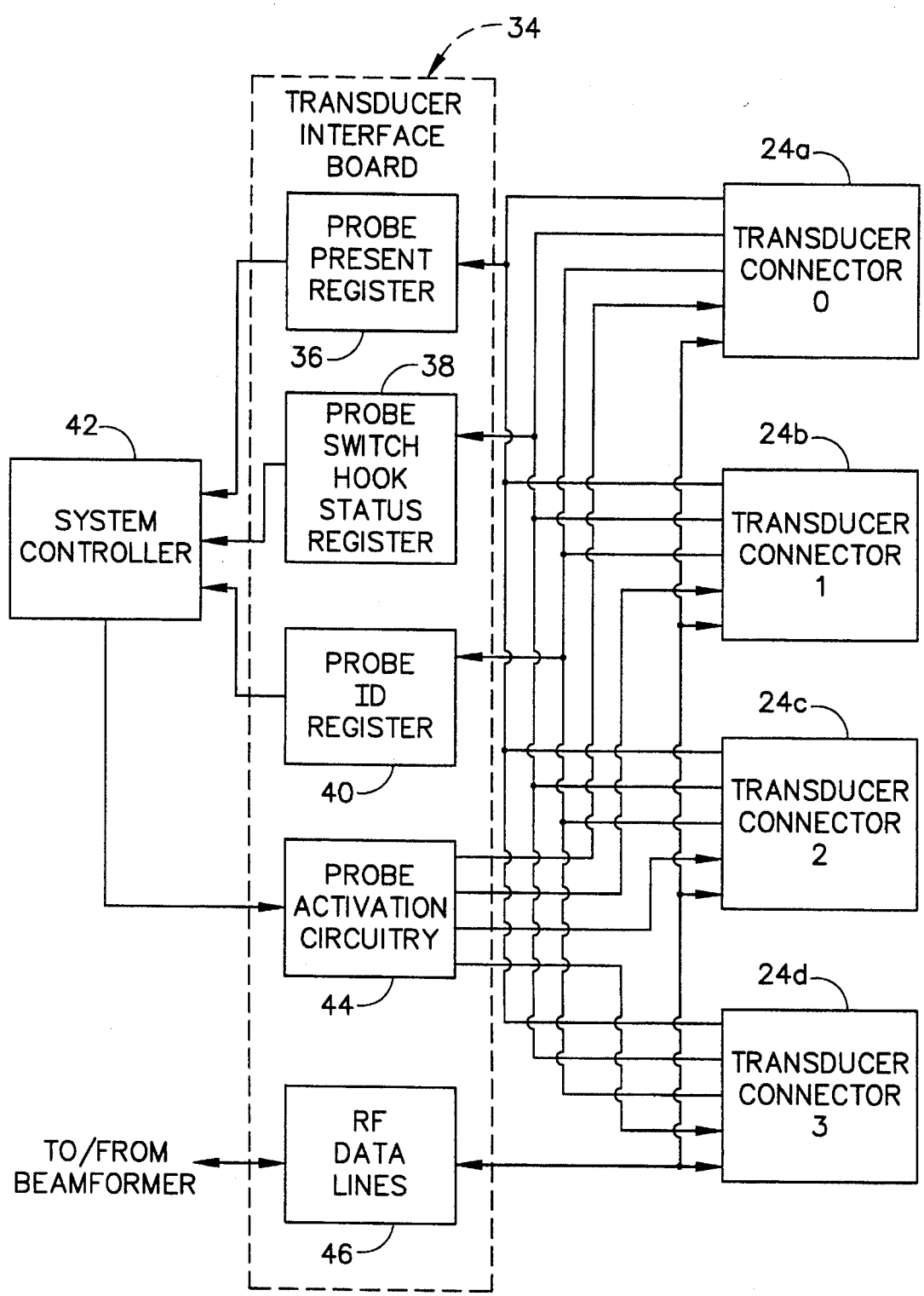
FIG. 4 is a circuit schematic for the probe present switch incorporated in the integral yoke/transducer connector depicted in FIG. 3.

Referring to FIG. 4, after power for the system has been turned on (step 60), the system controller periodically (as the result of a software interrupt) reads the contents of probe present register 46 and probe switch hook status register 48 to determine whether any change in the status of the transducers has occurred (step 61). Four changes are possible: a transducer has been connected to the system (step 62); a transducer has been disconnected from the system (step 63); a connected transducer has been taken out of its holder (step 64); or a connected transducer has been put in its holder (step 65).

If the system controller determines that a transducer has been connected to the system (step 62), the system controller reads the contents of the probe ID register 50 and determines whether the connected transducer is normal or special (step 66). If the probe ID indicates that the transducer is special, the system controller checks whether there is presently an active transducer (step 67). If an active transducer is present, the system controller determines whether the active transducer is normal or special (step 68). If the active transducer is normal, the identifier for the connected transducer is stored in the stack below the identifiers for all normal transducers (step 69). Then the selection routine returns to the main program until the next software interrupt (step 61).

If the system controller determines in step 68 that the active transducer is special, then the identifier for the active transducer is stored in the stack below the identifiers for all normal transducers (step 70). Following step 70, the connected transducer is activated (step 71). The connected transducer is also activated if during step 67 the system controller determines that there is no active transducer. Then the selection routine returns to the main program until the next software interrupt (step 61).

Returning to step 66, if the system controller determines that the connected transducer is normal, then a determination is made whether the connected transducer is in or out of its holder (step 72). If the connected transducer is in its holder, then the selection routine returns to the main program until the next software interrupt. On the other hand, if the connected transducer is out of its holder, the system controller again checks whether there is presently an active transducer (step 73). If an active transducer is present, the system controller determines whether the active transducer is normal or special (step 74). If the active transducer is normal, the identifier for the connected transducer is stored at the top of the stack (step 75). Then the selection routine returns to the main program until the next software interrupt.

If the system controller determines in step 74 that the active transducer is special, then the identifier for the active transducer is stored in the stack below the identifiers for all normal transducers (step 70). Following step 70, the connected transducer is activated (step 71). The connected transducer is also activated if during step 73 the system controller determines that there is no active transducer. Then the selection routine returns to the main program until the next software interrupt.

If the system controller determines that a transducer has been taken out of its holder (step 64), the system controller determines whether that transducer is the active transducer (step 81). If the active transducer has been taken out of its holder, the system controller determines whether the image has been frozen (step 82). If it has, the image is then unfrozen (step 83) and the selection routine returns to the main program. If the image is not frozen, the selection routine returns to the main program.

If the transducer taken out of its holder was not the active transducer, the system controller again checks whether there is presently an active transducer (step 73). If an active transducer is present, the system controller determines whether the active transducer is normal or special (step 74). If the active transducer is normal, the identifier for the taken-out-of-holder transducer is stored at the top of the stack (step 75). Then the selection routine returns to the main program until the next software interrupt.

If the system controller determines in step 74 that the active transducer is special, then the identifier for the active transducer is stored in the stack below the identifiers for all normal transducers (step 70). Following step 70, the taken-out-of-holder transducer is activated (step 71). The taken-out-of-holder transducer is also activated if during step 73 the system controller determines that there is no active transducer. Then the selection routine returns to the main program until the next software interrupt.

If the system controller determines that a transducer has been disconnected from the system (step 63), the system controller determines whether the active transducer has been disconnected (step 76). If the active transducer has been disconnected, the system controller determines whether the stack contains the identifier of a transducer (step 77). If not, the system is set to no active transducer (step 78) and the selection routine returns to the main program. Conversely, if the system controller determines that there is a probe identifier in the stack (step 77), then the transducer whose identifier is at the top of the stack is activated (step 79). After transducer activation, the selection routine returns to the main program.

If the disconnected transducer was not the active transducer, the identifier of the disconnected transducer, if present, is removed from the stack (step 80). Then the selection routine returns to the main program until the next software interrupt.

If the system controller determines that a transducer has been put in its holder (step 65), the system controller determines whether that transducer is the active transducer (step 84). If the active transducer has been put in its holder, the system controller determines whether there is a probe identifier in the stack (step 85). If the stack contains no transducer identifier, then the image is frozen (step 86). If the system controller determines that there is a probe identifier in the stack (step 85), then the transducer whose identifier is at the top of the stack is activated (step 79). After transducer activation, the selection routine returns to the main program.

Referring to step 84, if the put-in-its-holder transducer is not the active transducer, the identifier of the put-in-its-holder transducer, if present, is removed from the stack (step 80). Then the selection routine returns to the main program until the next software interrupt.

In accordance with the above-described sequence of steps, selection of a connected transducer probe for activation is performed automatically by the system controller in dependence on feedback indicating which transducers are connected and which connected transducers have been removed from their respective holders. This automatic process eliminates the need for the user to press a button or key to activate a desired transducer probe.

The foregoing preferred embodiment has been disclosed for the purpose of illustration. Variations and modifications will be readily apparent to those skilled in the art of ultrasound imaging systems. All such variations and modifications are intended to be encompassed by the claims set forth hereinafter.

We claim:

1. An ultrasound imaging system comprising:

a plurality of transducer probe assemblies, each transducer probe assembly comprising a normal transducer, a transducer connector and means for generating a signal containing a probe identifier identifying the type of normal transducer;

a plurality of ports for respectively coupling with a respective one of said transducer connectors;

a plurality of transducer holders, each transducer holder being configured to hold a respective one of said normal transducers;

means for activating a selected one of said normal transducers; and processing means for stacking the probe identifiers of any unactivated connected normal transducers which are out of their respective holders, said probe identifiers being stacked in an order which is determined by the order in which said unactivated connected normal transducers become both connected and out of their respective holder.

2. The ultrasound imaging system as defined in claim 1, wherein each transducer connector has means for generating a probe present signal indicating connection of said connector to a port, further comprising means for generating respective probe hook status signals indicating which of said normal transducers are being held by a respective holder, and a transducer interface comprising a first register for storing said probe identifiers, a second register for storing said probe present signals and a third register for storing said probe switch hook status signals.

3. The ultrasound imaging system as defined in claim 2, further comprising means for periodically reading the contents of said first through third registers, said processing means stacking said probe identifiers in an order dependent on said probe present signals and said probe switch hook status signals.

4. The ultrasound imaging system as defined in claim 1, wherein said processing means comprises means for adding a first probe identifier to the top of said stack in response to a first normal transducer identified by said first probe identifier being removed from a first holder, if said first normal transducer is connected and a second normal transducer is active, or in response to said first normal transducer being connected to said system, if said first normal transducer is out of its holder and said second normal transducer is active.

5. The ultrasound imaging system as defined in claim 1, wherein in response to a first normal transducer identified by a first probe identifier being connected to said system while said first normal transducer is seated in a first holder, said processing means does not add said first probe identifier to the top of said stack.

6. The ultrasound imaging system as defined in claim 1, wherein said processing means comprises means for removing a first probe identifier from the top of said stack in response to the normal transducer identified by said first probe identifier being disconnected from said system or put in its holder while not activated.

7. The ultrasound imaging system as defined in claim 1, wherein said processing means comprises means for controlling said activating means to activate a first normal transducer identified by a first probe identifier at the top of said stack in response to a second normal transducer identified by a second probe identifier being disconnected from said system or put in its holder while activated.

8. The ultrasound imaging system as defined in claim 1, further comprising a first special transducer having means for generating a signal containing a first probe identifier identifying said first special transducer, wherein said processing means comprises means for adding said first probe identifier to said stack below any probe identifiers for normal transducers if said first special transducer is connected to said system while a first normal transducer is active.

9. The ultrasound imaging system as defined in claim 1, further comprising a first special transducer having means for generating a signal containing a first probe identifier identifying said first special transducer and a second special transducer having means for generating a signal containing a second probe identifier identifying said second special transducer, wherein said processing means comprises means for adding said second probe identifier to said stack below any probe identifiers for normal transducers if said first special transducer is connected to said system while said second special transducer is active.

10. The ultrasound imaging system as defined in claim 1, further comprising a first special transducer having means for generating a signal containing a first probe identifier identifying said first special transducer, wherein said processing means comprises means for adding said first probe identifier to said stack below any probe identifiers for normal transducers in response to a first normal transducer being connected to said system if said first normal transducer is out of its holder and said first special transducer is active.

11. An ultrasound imaging system comprising:
a plurality of transducer probe assemblies, each transducer probe assembly comprising a transducer, a transducer connector and means for generating a signal containing a probe identifier identifying the type of transducer, each of said transducers being either a normal transducer or a special transducer;
a plurality of ports for respectively coupling with a respective one of said transducer connectors;
a plurality of transducer holders, each transducer holder being configured to hold a respective one of said transducers;

means for activating a selected one of said transducers; and processing means for stacking the probe identifiers of any unactivated connected normal transducers which are out of their respective holders and any unactivated connected special transducers, said probe identifiers being stacked in an order reflecting relative activation priorities of said unactivated connected normal transducers which are out of their respective holders and said unactivated connected special transducers, wherein said processing means comprise means for controlling said activating means to activate a selected transducer identified by the probe identifier at the top of said stack in response to deactivation of a presently active transducer.

12. The ultrasound imaging system as defined in claim 11, wherein each transducer connector has means for generating a probe present signal indicating connection of said connector to a port, further comprising:
means for generating respective probe hook status signals indicating which of said normal transducers are being held by a respective holder;
a transducer interface comprising a first register for storing said probe identifiers, a second register for storing said probe present signals and a third register for storing said probe switch hook status signals; and
means for periodically reading the contents of said first through third registers,
wherein said processing means stacks said probe identifiers of any unactivated connected normal transducers which are out of their respective holders and any unactivated connected special transducers in an order dependent on whether said transducer is normal or special and in dependence on the order in which said unactivated connected normal transducers become both connected and out of their respective holder and said unactivated special transducers become connected.

13. The ultrasound imaging system as defined in claim 11, wherein said processing means comprises means for adding a first probe identifier to the top of said stack in response to a first normal transducer identified by said first probe identifier being removed from a first holder, if said first normal transducer is connected and a second normal transducer is active, or in response to said first normal transducer being connected to said system, if said first normal transducer is out of its holder and said second normal transducer is active.

14. The ultrasound imaging system as defined in claim 11, wherein in response to a first normal transducer identified by a first probe identifier being connected to said system while said first normal transducer is seated in a first holder, said processing means does not add said first probe identifier to the top of said stack.

15. The ultrasound imaging system as defined in claim 11, wherein said processing means comprises means for removing a first probe identifier from the top of said stack in response to the normal transducer identified by said first probe identifier being disconnected from said system or put in its holder while not activated.

16. The ultrasound imaging system as defined in claim 11, wherein said processing means comprises means for controlling said activating means to activate a first normal transducer identified by a first probe identifier at the top of said stack in response to a second normal transducer identified by a second probe identifier being disconnected from said system or put in its holder while activated.

17. The ultrasound imaging system as defined in claim 11, comprising a first special transducer having means for generating a signal containing a first probe identifier identifying said first special transducer, wherein said processing means comprises means for adding said first probe identifier to said stack below any probe identifiers for normal transducers if said first special transducer is connected to said system while a first normal transducer is active.

18. The ultrasound imaging system as defined in claim 11, comprising a first special transducer having means for generating a signal containing a first probe identifier identifying said first special transducer and a second special transducer having means for generating a signal containing a second probe identifier identifying said second special transducer, wherein said processing means comprises means for adding said second probe identifier to said stack below any probe identifiers for normal transducers if said first special transducer is connected to said system while said second special transducer is active.

19. The ultrasound imaging system as defined in claim 11, comprising a first special transducer having means for generating a signal containing a first probe identifier identifying said first special transducer, wherein said processing means comprises means for adding said first probe identifier to said stack below any probe identifiers for normal transducers in response to a first normal transducer being connected to said system if said first normal transducer is out of its holder and said first special transducer is active.

20. A method for selecting a transducer for activation in an ultrasound imaging system having a plurality of transducers respectively coupled to a plurality of ports by way of a respective plurality of transducer connectors and respectively supported by a plurality of yokes, each of said transducers being either a normal transducer or a special transducer, comprising the steps of:

for each coupled transducer probe, generating a signal containing a probe identifier identifying the type of transducer;

arranging a stack of probe identifiers of any unactivated connected normal transducers which are out of their respective holders and any unactivated connected special transducers, said probe identifiers being stacked in an order reflecting relative activation priorities of said unactivated connected normal transducers which are out of their respective holders and said unactivated connected special transducers; and activating a selected transducer identified by the probe identifier at the top of said stack in response to deactivation of a presently active transducer.

* * * * *